United States Patent
Kitane et al.

(10) Patent No.: US 8,508,223 B2
(45) Date of Patent: Aug. 13, 2013

(54) NON-CONTRAST MRA USING REGION-SELECTIVE SATURATION PULSE FOLLOWED BY NON-REGION SELECTIVE INVERSION RECOVERY PULSE TO LARGER OVERLAPPED AREA

(75) Inventors: Shinichi Kitane, Nasushiobara (JP); Tokunori Kimura, Yaita (JP); Yuichi Yamashita, Otawara (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 459 days.

(21) Appl. No.: 12/751,128

(22) Filed: Mar. 31, 2010

(65) Prior Publication Data

US 2011/0074417 A1 Mar. 31, 2011

(30) Foreign Application Priority Data

Sep. 30, 2009 (JP) ................................ 2009-228318

(51) Int. Cl.
*G01V 3/00* (2006.01)

(52) U.S. Cl.
USPC .......................................................... 324/307

(58) Field of Classification Search
USPC .................................................. 324/300–322
See application file for complete search history.

(56) References Cited

U.S. PATENT DOCUMENTS

| 6,782,286 B2 * | 8/2004 | Miyazaki | 600/410 |
| 7,564,240 B2 * | 7/2009 | Ganesan | 324/303 |
| 7,623,901 B2 * | 11/2009 | Kanazawa | 600/413 |
| 2009/0062640 A1 | 3/2009 | Miyoshi | |

FOREIGN PATENT DOCUMENTS

JP 2009-28525 2/2009

OTHER PUBLICATIONS

Dixon et al., "Multiple Inversion Recovery Reduces Static Tissue Signal in Angiograms", Magnetic Resonance in Medicine 18, pp. 257-268, (1991).

* cited by examiner

*Primary Examiner* — Dixomara Vargas
(74) *Attorney, Agent, or Firm* — Nixon & Vanderhye PC

(57) ABSTRACT

A magnetic resonance imaging (MRI) apparatus acquires magnetic resonance (MR) data associated with a plurality of different delay times according to a pulse sequence in which a region-selective saturation pulse is first applied, a region-non-selective inversion recovery pulse is then applied, and then the magnetic resonance data is acquired, the delay time being defined as a period from the saturation pulse application time to the start of MR data acquisition. A plurality of blood flow image data respectively associated with the plurality of different delay times are created using the acquired MR data.

18 Claims, 13 Drawing Sheets

SAT PULSE ×2
(B)

SAT PULSE ×1
(A)

NON-CONTRAST MRA USING REGION-SELECTIVE SATURATION PULSE FOLLOWED BY NON-REGION SELECTIVE INVERSION RECOVERY PULSE TO LARGER OVERLAPPED AREA

This application claims priority to Japanese Application No(s). 2009-228318, filed 30 Sep. 2009, the entire content of which is hereby incorporated by reference.

BACKGROUND

1. Technical Field

The present document relates to a magnetic resonance imaging (MRI) apparatus that magnetically excites a nuclear spin in a subject body with a radio frequency (RF) signal at the Larmor frequency and reconstructs an image from a nuclear magnetic resonance (NMR) signal yielded as a result of the excitement, and control method thereof. In particular, it relates to a magnetic resonance imaging apparatus capable of non-contrast magnetic resonance angiography (MRA), which produces a blood flow image without using a contrast medium and control method thereof.

2. Related Art

Magnetic resonance imaging is an imaging technique that magnetically excites nuclear spin in a subject body laid in a static magnetic field with an RF signal at the Larmor frequency and reconstructs an image from an MR signal yielded as a result of the excitement.

In the field of magnetic resonance imaging, the arterial spin labeling (ASL) technique is a known technique of producing a blood flow image in a non-contrast manner (see Patent Document 1 (Japanese Patent Laid-Open No. 2009-28525), for example). The ASL technique is to render an image of a blood flow by labeling blood by applying an ASL pulse. As is known, in the ASL technique, a background signal can be suppressed by performing subtraction between image data acquired by using the blood labeling and image data acquired without using the blood labeling.

SUMMARY

However, the conventional ASL-based non-contrast MRA has the following problems. (1) To suppress the background signal, imaging has to be performed twice, leading to an elongated imaging time, (2) Because of the elongated imaging time, the background signal sometimes cannot be sufficiently suppressed because of motion of a subject body or misregistration. (3) A temporal change of blood cannot be observed.

The present exemplary embodiment has been devised to cope with the problems of the conventional technique, and an object of the present exemplary embodiment is to provide a magnetic resonance imaging apparatus capable of acquiring a non-contrast MRA image in which a background signal is sufficiently suppressed in a shorter time.

Another object of the present exemplary embodiment is to provide a magnetic resonance imaging apparatus capable of acquiring a non-contrast MRA image in which a temporal change of blood can be observed.

In order to attain the objects described above, a magnetic resonance imaging apparatus according to the present exemplary embodiment includes: a data acquiring unit that acquires a plurality of pieces of magnetic resonance data associated with a plurality of different delay times according to a pulse sequence in which a region-selective saturation pulse is first applied, a region-non-selective inversion recovery pulse is then applied, and then the magnetic resonance data is acquired, the delay time being defined as a period from a time of application of the saturation pulse to a time of start of acquisition of the magnetic resonance data; and a blood flow image creating unit that creates a plurality of pieces of blood flow image data associated with the plurality of different delay times using the magnetic resonance data.

Further, in order to attain the objects described above, a control method of a magnetic resonance imaging apparatus according to the present exemplary embodiment includes: acquiring a plurality of pieces of magnetic resonance data associated with a plurality of different delay times according to a pulse sequence in which a region-selective saturation pulse is first applied, a region-non-selective inversion recovery pulse is then applied, and then the magnetic resonance data is acquired, the delay time being defined as a period from a time of application of the saturation pulse to a time of start of acquisition of the magnetic resonance data; and creating a plurality of pieces of blood flow image data associated with the plurality of different delay times using the magnetic resonance data.

The magnetic resonance imaging apparatus according to the present exemplary embodiment can acquire a non-contrast MRA image in which a background signal is sufficiently suppressed in a shorter time.

The magnetic resonance imaging apparatus according to the present exemplary embodiment can acquire a non-contrast MRA image in which a temporal change of blood can be observed.

DETAILED DESCRIPTION

A magnetic resonance imaging apparatus according to an embodiment of the present invention will be described with reference to the accompanying drawings.

(Configuration and Function)

Figure 1:
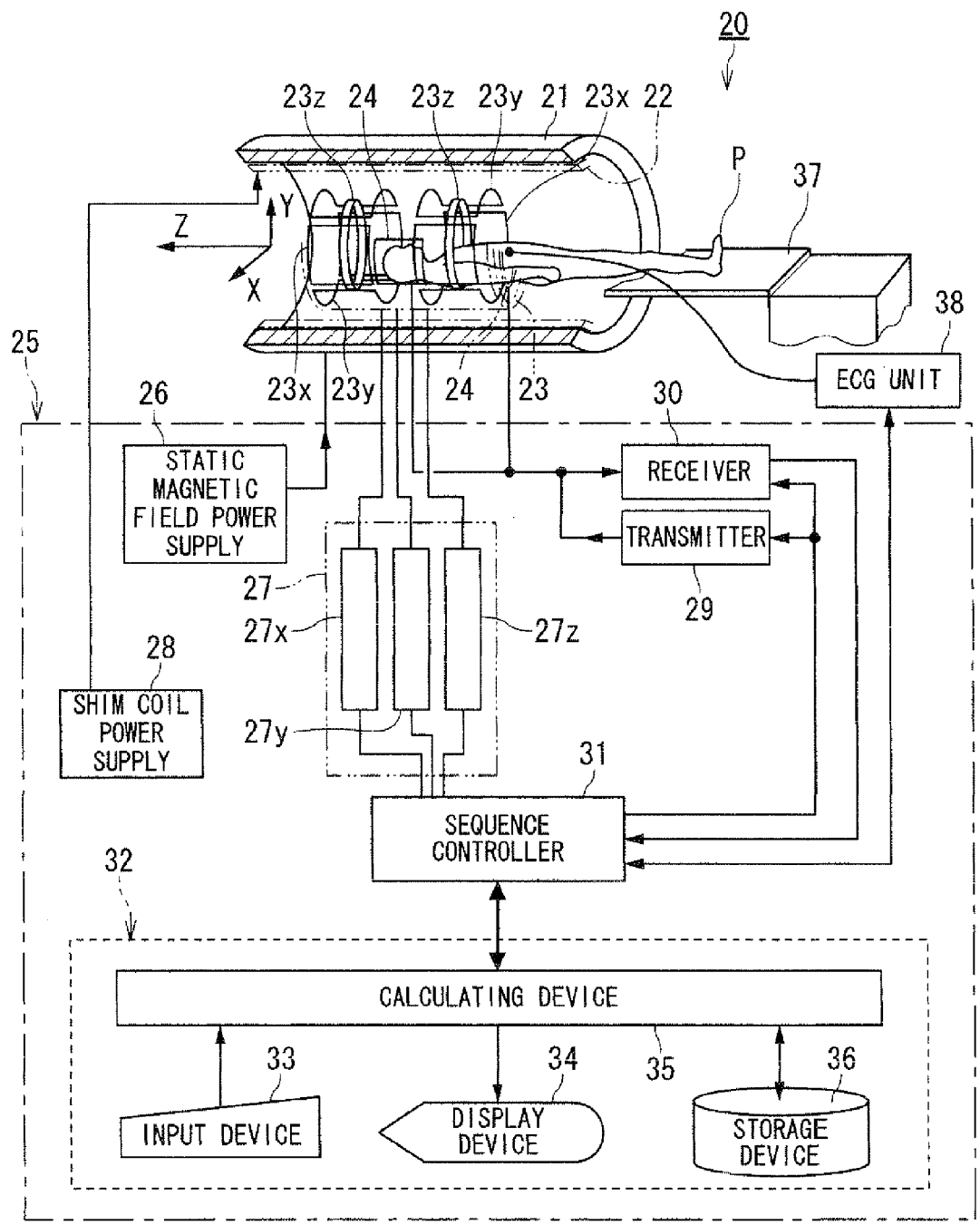
FIG. 1 is a diagram showing a configuration of a magnetic resonance imaging apparatus according to an embodiment of the present invention.

FIG. 1 is a diagram showing a configuration of a magnetic resonance imaging apparatus according to an embodiment of the present invention.

A magnetic resonance imaging apparatus 20 comprises a static magnetic field magnet 21 that produces a static magnetic field, a shim coil 22 disposed in the static magnetic field magnet 21, gradient magnetic field coils 23, and RF coils 24.

The magnetic resonance imaging apparatus 20 further comprises a control system 25. The control system 25 comprises a static magnetic field power supply 26, a gradient magnetic field power supply unit 27, a shim coil power supply 28, a transmitter 29, a receiver 30, a sequence controller 31, and a computer 32. The gradient magnetic field power supply unit 27 of the control system 25 has an X-axis gradient magnetic field power supply 27x, a Y-axis gradient magnetic field power supply 27y, and a Z-axis gradient magnetic field power supply 27z. The computer 32 has an input device 33, a display device 34, a calculating device 35, and a storage device 36.

The static magnetic field magnet 21 is connected to the static magnetic field power supply 26 and has a function of producing a static magnetic field in an imaging region when a current is supplied thereto from the static magnetic field power supply 26. Typically, the static magnetic field magnet 21 is a superconductive coil. Although the static magnetic field magnet 21 is connected to the static magnetic field power supply 26 and excited by the current supplied therefrom, the current is typically stopped once it is excited. Alternatively, the static magnetic field magnet 21 may be a permanent magnet. In this case, the static magnetic field power supply 26 is omitted.

The static magnetic field magnet 21 houses the shim coil 22, which has a tubular shape and is disposed coaxially with the static magnetic field magnet 21. The shim coil 22 is connected to the shim coil power supply 28 and serves to make the static magnetic field uniform when a current is supplied thereto from the shim coil 22.

The gradient magnetic field coils 23 include an X-axis gradient magnetic field coil 23x, a Y-axis gradient magnetic field coil 23y, and a Z-axis gradient magnetic field coil 23z. The gradient magnetic field coils 23 have a tubular shape and are disposed in the static magnetic field magnet 21. A bed 37, which is the imaging region, is disposed inside the gradient magnetic field coils 23, and a subject body P is laid on the bed 37. The RF coils 24 includes a whole body coil (WBC) for transmitting and receiving an RE signal incorporated in a gantry and a local coil for receiving an RF signal disposed close to the bed 37 or the subject body P, for example.

The gradient magnetic field coils 23 are connected to the gradient magnetic field power supply unit 27. Of the gradient magnetic field coils 23, the X-axis gradient magnetic field coil 23x, the Y-axis gradient magnetic field coil 23y and the Z-axis gradient magnetic field coil 23z are connected to the X-axis gradient magnetic field power supply 27x, the Y-axis gradient magnetic field power supply 27y and the Z-axis gradient magnetic field power supply 27z of the gradient magnetic power supply unit 27, respectively.

The X-axis gradient magnetic field coil 23x, the Y-axis gradient magnetic field coil 23y and the Z-axis gradient magnetic field coil 23z produce a gradient magnetic field Gx in the X axis direction, a gradient magnetic field Gy in the Y axis direction and a gradient magnetic field Gz in the Z axis direction in the imaging region, respectively, when a current is supplied thereto from the X-axis gradient magnetic field power supply 27x, the Y-axis gradient magnetic field power supply 27y and the Z-axis gradient magnetic field power supply 27z.

The RF coils 24 are connected to the transmitter 29 and/or the receiver 30. An RE coil 24 for transmission is supplied with an RE signal from the transmitter 29 and transmits the RE signal to the subject body P, and an RE coil 24 for reception receives an NMR signal yielded as a result of the excitation of a nuclear spin in the subject body by the RE signal and transferring the NMR signal to the receiver 30.

The sequence controller 31 in the control system 25 is connected to the gradient magnetic field power supply unit 27, the transmitter 29 and the receiver 30. The sequence controller 31 has a function of storing sequence information that describes control information required to drive the gradient magnetic field power supply unit 27, the transmitter 29 and the receiver 30, such as operation control information including the intensity, the duration, and the timing of the pulse current to be applied to the gradient magnetic field power supply unit 27. The sequence controller 31 also has a function of driving the gradient magnetic field power supply unit 27, the transmitter 29 and the receiver 30 according to the stored predetermined sequence to produce the X-axis gradient magnetic field Gx, the Y-axis gradient magnetic field Gy, the Z-axis gradient magnetic field Gz and the RF signal.

The sequence controller 31 receives raw data, which is complex data outputted from the receiver 30 by detecting the NMR signal and performing analog-to-digital (A/D) conversion on the NMR signal, and transmits the raw data to the computer 32.

The transmitter 29 has a function of generating RF signal based on the control information received from the sequence controller 31 and supplying the generated RF signal to the RF coil 24. On the other hand, the receiver 30 has a function of detecting the NMR signal received by the RF coil 24 and creating the raw data, which is digitalized complex data, by performing a required signal processing and A/D conversion on the detected NMR signal and a function of sending the created raw data to the sequence controller 31.

The magnetic resonance imaging apparatus 20 further comprises an electro cardiogram (ECG) unit 38 that acquires an ECG signal from the subject body P. The ECG signal acquired by the ECG unit 38 is output to the computer 32 via the sequence controller 31.

As an alternative to the ECG signal that represents pulsation in the form of heartbeat information, a peripheral pulse gating (PPG) signal that represents pulsation in the form of pulse wave information may be used. The PPG signal is a signal that is obtained by optically detecting a fingertip pulse wave, for example. In the case where the PPG signal is used, the magnetic resonance imaging apparatus 20 has a PPG signal detecting unit.

The storage device 36 of the computer 32 stores a program, and the calculating device 35 executes the program to make the computer 32 perform various functions. As an alternative to the program, the magnetic resonance imaging apparatus 20 may have specific circuits that perform the various functions.

Figure 2:
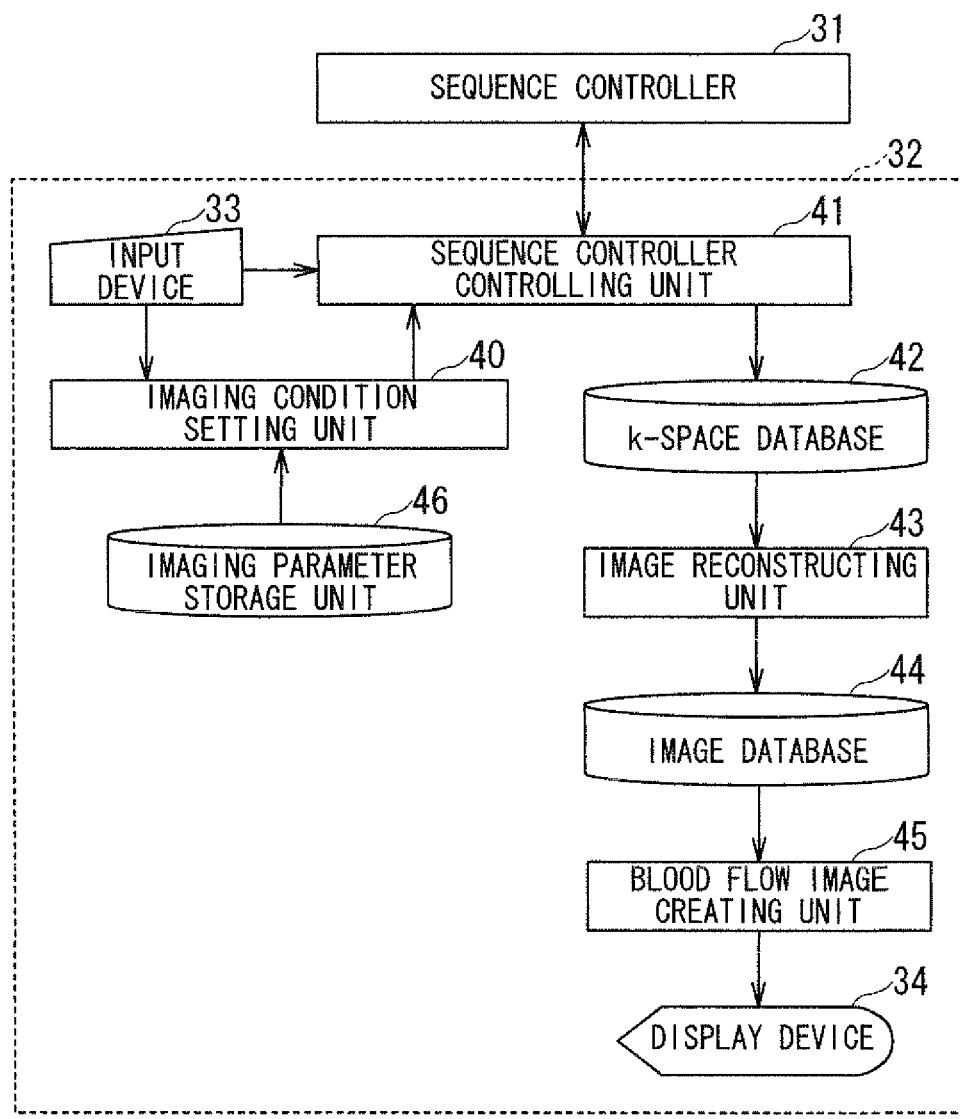
FIG. 2 is a functional block diagram showing a computer shown in FIG. 1.

FIG. 2 is a functional block diagram showing the computer 32 shown in FIG. 1.

Under the control of the program, the computer 32 functions as an imaging condition setting unit 40, a sequence controller controlling unit 41, a k-space database 42, an image reconstructing unit 43, an image database 44, a blood flow image creating unit 45, and an imaging parameter storage unit (a parameter storage unit) 46.

A data acquiring unit is configured to include at least the imaging condition setting unit 40, the sequence controller controlling unit 41, the k-space database 42, the an image reconstructing unit 43.

The imaging condition setting unit 40 has a function of setting an imaging condition including a pulse sequence based on instruction information from the input device 33 and transmitting the imaging condition to the sequence controller controlling unit 41. In particular, the imaging condition setting unit 40 has a function of setting an imaging condition for blood flow image acquisition as described later.

The imaging parameter storage unit 46 stores a control parameter for the image contrast that is required to set the imaging condition for blood flow image acquisition.

The sequence controller controlling unit 41 has a function of driving and controlling the sequence controller 31 by transmitting the imaging condition to the sequence controller 31 based on information from the input device 33 or other components. The sequence controller controlling unit 41 also has a function of receiving the raw data from the sequence controller 31 and placing the raw data as k-space data in the k-space database 42.

The image reconstructing unit 43 has a functions of reconstructing image data by retrieving the k-space data from the k-space database 42 and performing an image reconstruction processing including Fourier transform (FT) on the k-space data, and a function of writing the reconstructed image data in the image database 44.

The blood flow image creating unit 45 has a function of creating blood flow image data for display by reading required image data from the image database 44 and performing an image processing, such as a subtraction processing, and a display processing, such as a maximum intensity projection (MIP) processing, on the image data, and a function of displaying a blood flow image on the display device 34 by sending the created blood flow image data to the display device 34.

(Operation and Effect)

Next, an operation and an effect of the magnetic resonance imaging apparatus 20 will be described.

Figure 3:
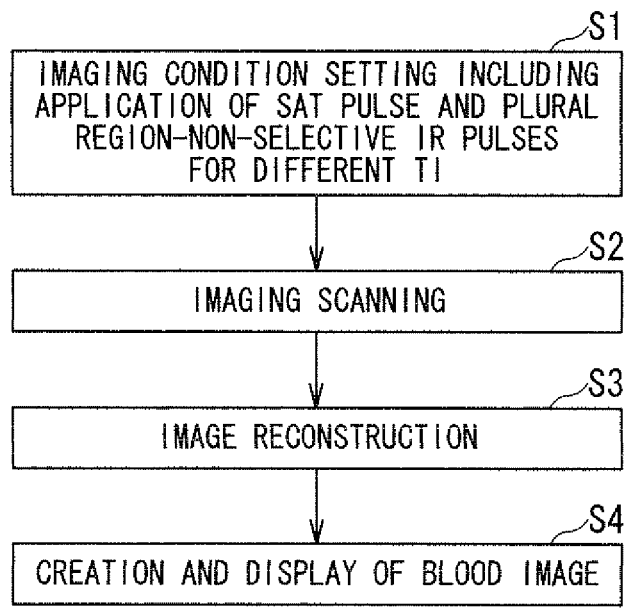
FIG. 3 is a flow chart showing a process of imaging a blood flow in a subject body in a non-contrast manner by the magnetic resonance imaging apparatus shown in FIG. 1.

FIG. 3 is a flow chart for illustrating a process of the magnetic resonance imaging apparatus 20, shown in FIG. 1, in imaging a blood flow in the subject body P in a non-contrast manner.

First, in step S1, the imaging condition setting unit 40 sets an imaging condition including a pulse sequence for blood flow image data acquisition.

Figure 4:
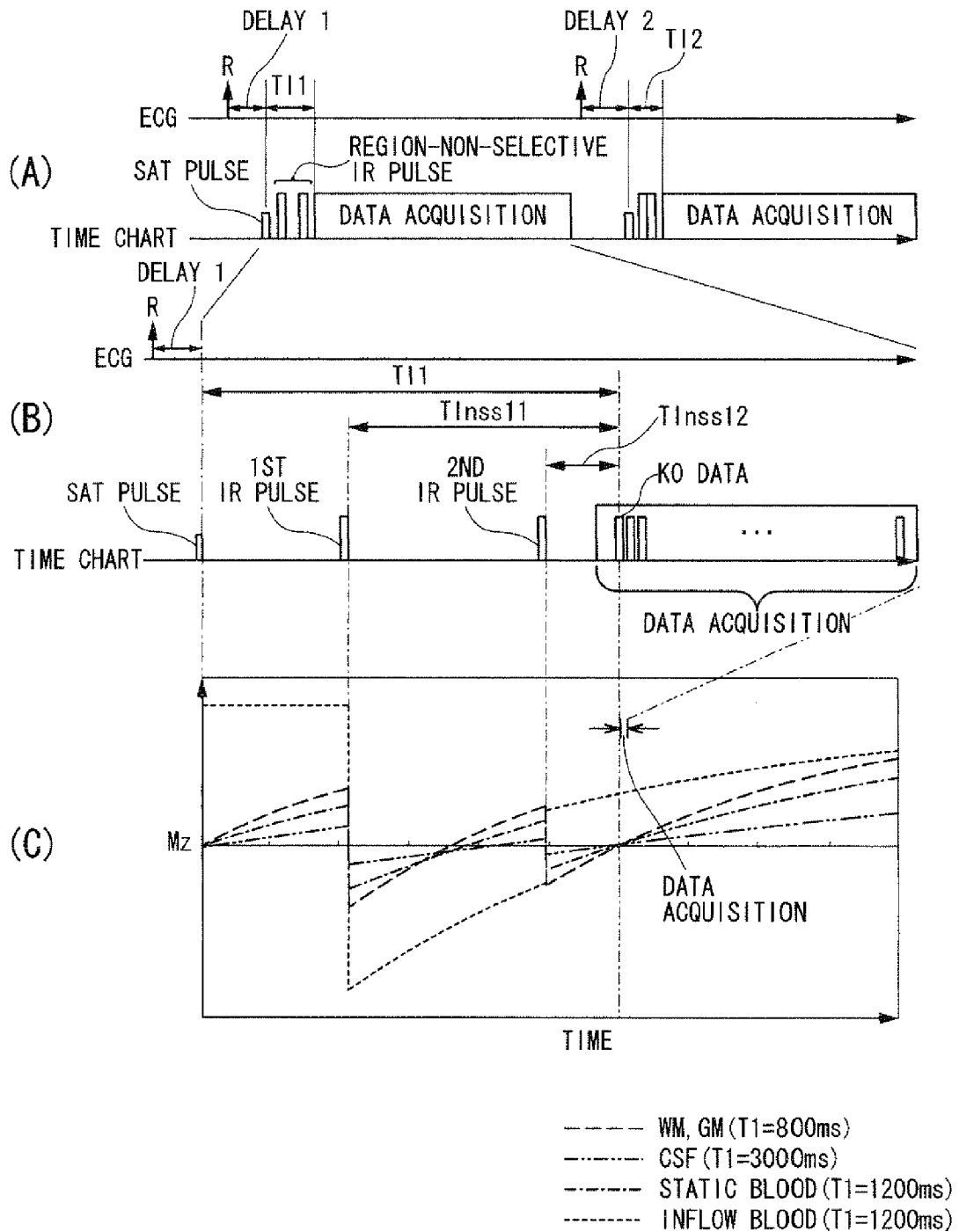
FIG. 4 includes diagrams for illustrating a pulse sequence for acquiring blood flow image data set in the magnetic resonance imaging apparatus shown in FIG. 1 and a temporal change in longitudinal magnetization.
Figure 5:
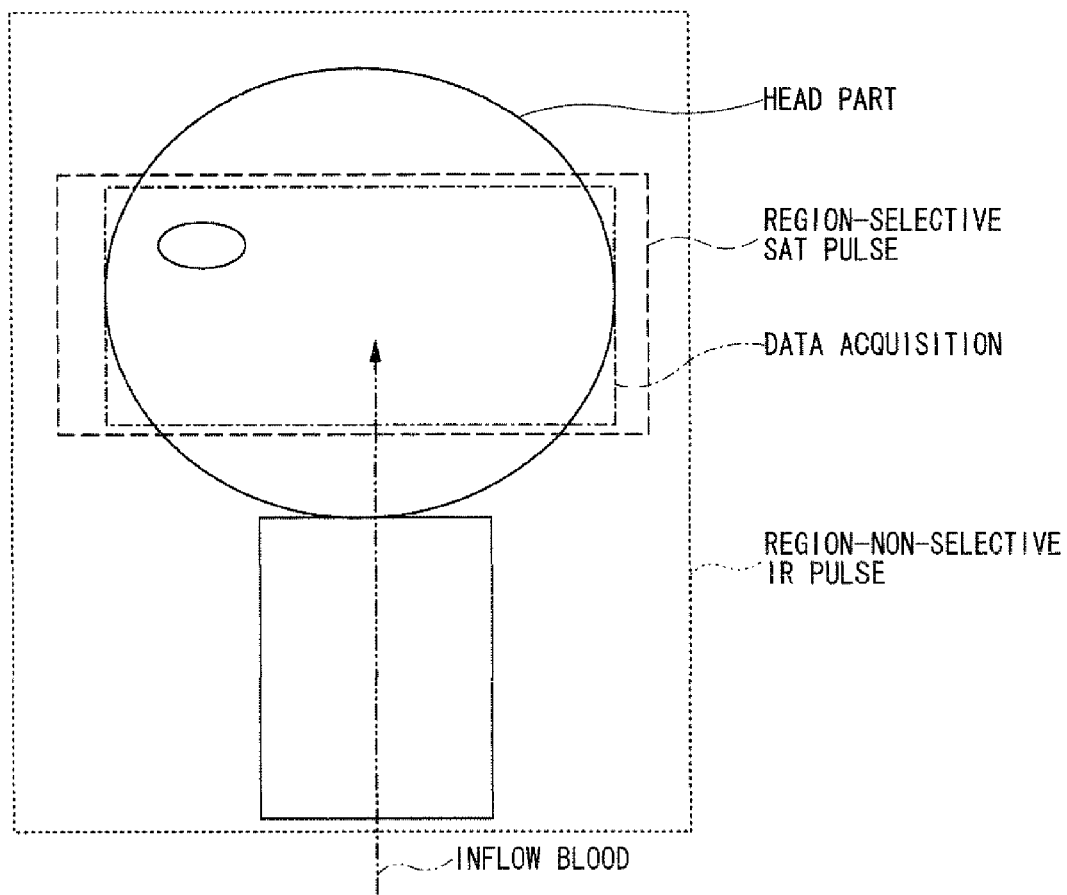
FIG. 5 is a diagram showing an application region of a SAT pulse shown in FIG. 4 and an imaging data acquisition region.

FIG. 4 includes time charts for illustrating the imaging condition for blood flow image data acquisition set in the magnetic resonance imaging apparatus 20 shown in FIG. 1. FIG. 5 is a diagram showing a region to which a SAT pulse shown in FIG. 4 is applied and a region in which data for imaging is acquired.

As shown in FIG. 4(A), a region-selective saturation (SAT) pulse synchronized with the ECG signal is first applied, one or more region-non-selective inversion recovery (IR) pulses are then applied, and then, a pulse sequence for data acquisition is set. The delay time TI is a time from the time of application of the SAT pulse to the start of data acquisition, and different delay times TI1, TI2, TI3 and so on may be set for different data acquisition processes. For example, the delay time TI may be set to gradually increase in an approximate range from 400 ms to 1600 ms each time data acquisition occurs. However, in the case where the segment k-space method is adopted, where the k-space is divided into several segments and the k-space data is acquired on a segment basis, the imaging condition is set so that the same delay time TI is repeatedly used for the segment-based data acquisition until the data in the k-space involved with the same cardiac time phase is completely acquired.

In addition, in order that the data is acquired in approximately the same cardiac time phase, the period from the occurrence of a reference wave, such as an R wave of the ECG signal, to the start of data acquisition is set to be constant. To achieve this, the delay times, such as DELAY1, DELAY2 and DELAY3, from the occurrence of the reference wave, such as the R wave, to the application of the SAT pulse are adjusted.

The SAT pulse application region is set in a region including the data acquisition region (imaging region) from which the blood flow image is to be extracted. FIG. 5 shows an example of the SAT pulse application region, which is set as a slab region in a head part of the subject body P that covers the data acquisition region. Alternatively, the SAT pulse application region may match to the data acquisition region.

FIG. 4(B) is an enlarged view of FIG. 4(A), and FIG. 4(C) is a diagram showing temporal changes in longitudinal magnetization before and after applications of the SAT pulse and the region-non-selective IR pulses shown in FIG. 4(B). As shown in FIG. 4(B), when a 90-degree SAT pulse is applied to the application region the delay time TI1 before the start of data acquisition, the magnetization vector in the application region falls by 90 degrees, and thus the longitudinal magnetization becomes 0. Then, the longitudinal magnetization of each substance is recovered with time at a rate depending on the longitudinal relaxation time (T1) that varies with the substance.

On the other hand, the blood that flows into the SAT pulse application region from outside as shown in FIG. 5 is not affected by the SAT pulse. Therefore, the normalized longitudinal magnetization of the blood flowing into the SAT pulse application region is 1. FIG. 4(C) shows temporal changes in longitudinal magnetization of a white matter (WM) and a gray matter (GM) having T1 of 800 ms, of a cerebrospinal fluid (CSF) having T1 of 3000 ms, of a static blood having T1 of 1200 ms that is affected by the SAT pulse in the SAT pulse application region, and of a blood having T1 of 1200 ms that flows into the SAT pulse application region.

Then, a first region-non-selective 180-degree IR pulse, which has an inversion time TInss11 before the start of data acquisition, is applied. As a result, as shown in FIG. 4(C), the magnetization vector in the whole of the head part including the blood flowing into the SAT pulse application region is inverted by 180 degrees and assumes a negative value. Then, the longitudinal magnetization of each substance is recovered with time again at a rate depending on T1.

Then, a second region-non-selective 180-degree IR pulse, which has an inversion time TInss12 before the start of data acquisition, is applied. As a result, as shown in FIG. 4(C), the magnetization vector in the whole of the head part is inverted by 180 degrees. It should be noted that, if the second region-non-selective 180-degree IR pulse is applied when the longitudinal magnetization of the blood flowing into the SAT pulse application region is negative, and the longitudinal magnetization of a major constituent to be suppressed is positive, the longitudinal magnetization of the blood flowing into the SAT pulse application region is inverted to a positive value, whereas the longitudinal magnetization of the constituent to be suppressed is inverted to a negative value.

As shown in FIG. 4(C), the imaging condition is set so that data acquisition from the data acquisition region shown in FIG. 5 starts when the absolute value of the longitudinal magnetization of the major constituent to be suppressed is at the minimum (substantially equals to zero) after the second 180-degree region-non-selective IR pulse is applied. The pulse sequence for data acquisition can be any sequence, such as a 3D balanced steady state free precession (SSFP) sequence. In the example shown in FIG. 4(C), the time of the start of data acquisition is set so that signals mainly involved with the white matter and the gray matter in the brain are selectively suppressed. Thus, data can be acquired in which the background signals are suppressed, and the signals involved with the blood flowing into the SAT pulse application region are selectively emphasized.

In other words, the number of the region-non-selective IR pulses to be applied and the period from the time of application of each region-non-selective IR pulse to the time of start of data acquisition (in other words, the optimal inversion time) are determined so that signals involved with tissues or other constituents to be suppressed are selectively suppressed when the data acquisition starts.

In principle, if one kind of tissue (suppression target tissue) is to be suppressed, application of one region-non-selective IR pulse suffices, and the optimal inversion time of the region-non-selective IR pulse can be determined from the set delay time and the longitudinal relaxation time of the suppression target tissue.

If there is a plurality of suppression target tissues, in general, a plurality of region-non-selective IR pulses is required to eliminate the longitudinal magnetization of all the tissues at the start of data acquisition, because each tissue has a different longitudinal relaxation time. That is, depending on the number of suppression target tissues, one or three or more region-non-selective IR pulses can be applied. However, according to the longitudinal magnetization change simulation, two region-non-selective IR pulses are preferably applied.

The imaging condition is set so that similar data acquisition is repeatedly performed for other different delay time TIn. If an optimal combination of inversion times (TInssn1, TInssn2, TInssn3 and so on) of the region-non-selective IR pulses for the delay time Tin for the n-th SAT pulse is previously determined by analysis, simulation or validation test, and stored in a database, the optimal inversion time of each region-non-selective IR pulse can be easily determined by referring to the database in setting of the imaging condition.

For this purpose, the imaging parameter storage unit 46 stores combinations of optimal inversion times (TInssn1, TInssn2 and so on) of region-non-selective IR pulses suitable for the respective delay times TI of the SAT pulses. When a plurality of different SAT pulse delay times TI is set, the imaging condition setting unit 40 automatically sets a combination of optimal inversion times (TInssn1, TInssn2 and so on) of the region-non-selective IR pulses for each SAT pulse delay time TI by referring to the imaging parameter storage unit 46. Alternatively, the optimal inversion times of the region-non-selective IR pulses can also be manually set by an operator through the input device 33. The combination of the optimal inversion times of the region-non-selective IR pulses for each SAT pulse delay time TI varies also with the longitudinal relaxation time T1 of a constituent of the site to be imaged. Thus, an appropriate combination of optimal inversion times of the region-non-selective IR pulses can also be previously determined for each site to be imaged, and the imaging parameter storage unit 46 can store the combinations.

As can be seen from the above description, owing to the region-non-selective IR pulses applied after application of the SAT pulse, the delay time TI from the time of application of the SAT pulse to the start of data acquisition can be longer than the inversion recovery times of the longitudinal magnetization of the unwanted constituents. More specifically, when the delay time TI is long, the longitudinal magnetization of an unwanted constituent having a short longitudinal relaxation time T1 is generally recovered to become large. However, according to this embodiment, since the region-non-selective IR pulses are applied, the recovered longitudinal magnetization of the unwanted constituent can be reduced to close to zero, and thus, the background signals can be suppressed.

In order to effectively suppress the background signals, the time of acquisition of data K0 DATA at the center of the k-space, which has a significant effect on the contrast, is preferably regarded as the time of the start of data acquisition that allows the longitudinal magnetization of the unwanted constituent to be brought close to zero. In addition, if the data K0 DATA at the center of the k-space is acquired in the same cardiac time phase in every data acquisition, the brightness of the blood part can be made uniform among different delay times TI. In addition, if the period between the occurrence of the reference wave, such as the R wave of the ECG signal, and the time of acquisition of the data K0 DATA at the center of the k-space is fixed as described above, data acquisitions can always be performed at the timing when the same amount of blood flows.

Then, in step S2 of FIG. 3, imaging scanning is performed according to the set imaging condition.

To achieve this, the subject body P is laid on the bed 37 in advance, and the static magnetic field magnet 21 (superconductive magnet) excited by the static magnetic field power supply 26 produces a static magnetic field in the imaging region. In addition, the shim coil 22 receives a current from the shim coil power supply 28 to make the static magnetic field produced in the imaging region uniform.

Then, in response to a scan start instruction issued from the input device 33, the sequence controller controlling unit 41 transmits the imaging condition including the pulse sequence obtained from the imaging condition setting unit 40 to the sequence controller 31. The sequence controller 31 drives the gradient magnetic field power supply unit 27, the transmitter 29 and the receiver 30 according to the pulse sequence received from the sequence controller controlling unit 41 to produce a gradient magnetic field in the imaging region in which the subject body P is laid and make the RF coil 24 produce an RF signal.

Then, an NMR signal is yielded from the subject body P as a result of nuclear magnetic resonance, and the RF coil 24 receives the NMR signal and transmits the NMR signal to the receiver 30. The receiver 30 performs a required signal processing and A/D conversion on the NMR signal received from the RF coil 24 to create raw data, which is the digitalized NMR signal. The receiver 30 transmits the created raw data to the sequence controller 31. The sequence controller 31 transmits the raw data to the sequence controller controlling unit 41, and the sequence controller controlling unit 41 places the raw data as k-space data in the k-space formed in the k-space database 42.

The data acquisition described above is repeatedly performed at intervals of different delay times TI in synchronization with the ECG signal acquired by the ECG unit 38.

Therefore, the k-space database 42 stores k-space data for each of the different delay times TI.

Then, in step S3, the image reconstructing unit 43 creates image data for each delay time TI by performing an image reconstruction processing on the k-space data retrieved from the k-space database 42 and writes the created image data to the image database 44.

Then, in step S4, the blood flow image creating unit 45 reads the image data for each delay time TI from the image database 44 and creates blood flow image data for display by performing a required image processing, such as an MIP processing. The display device 34 displays the crated blood flow image data for each delay time TI.

Figure 6:
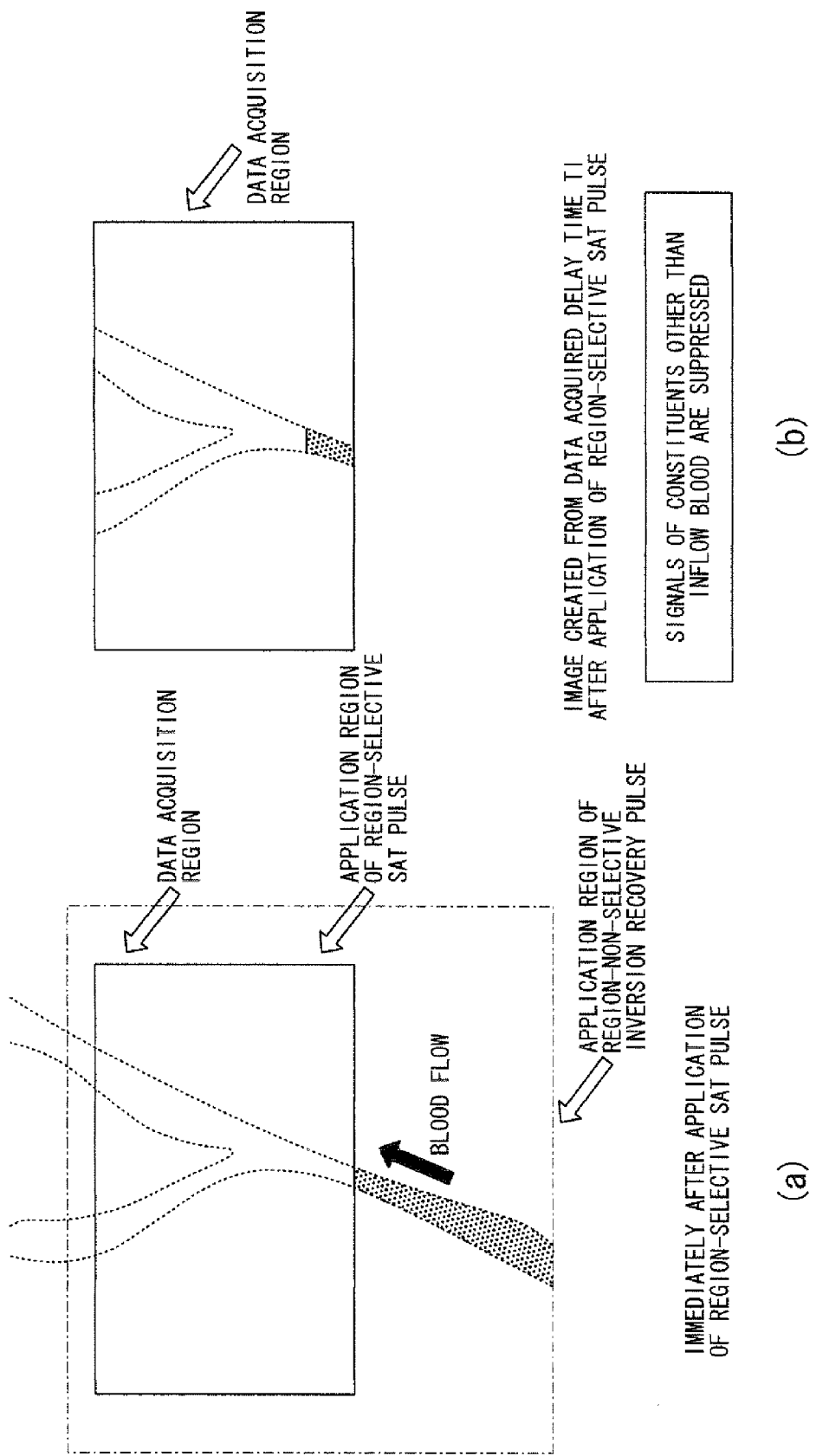
FIG. 6 shows a schematic blood flow image created from data acquired immediately after application of a region-selective saturation pulse and a schematic blood flow image created from data acquired a delay time after the application of the region-selective saturation pulse.
Figure 7:
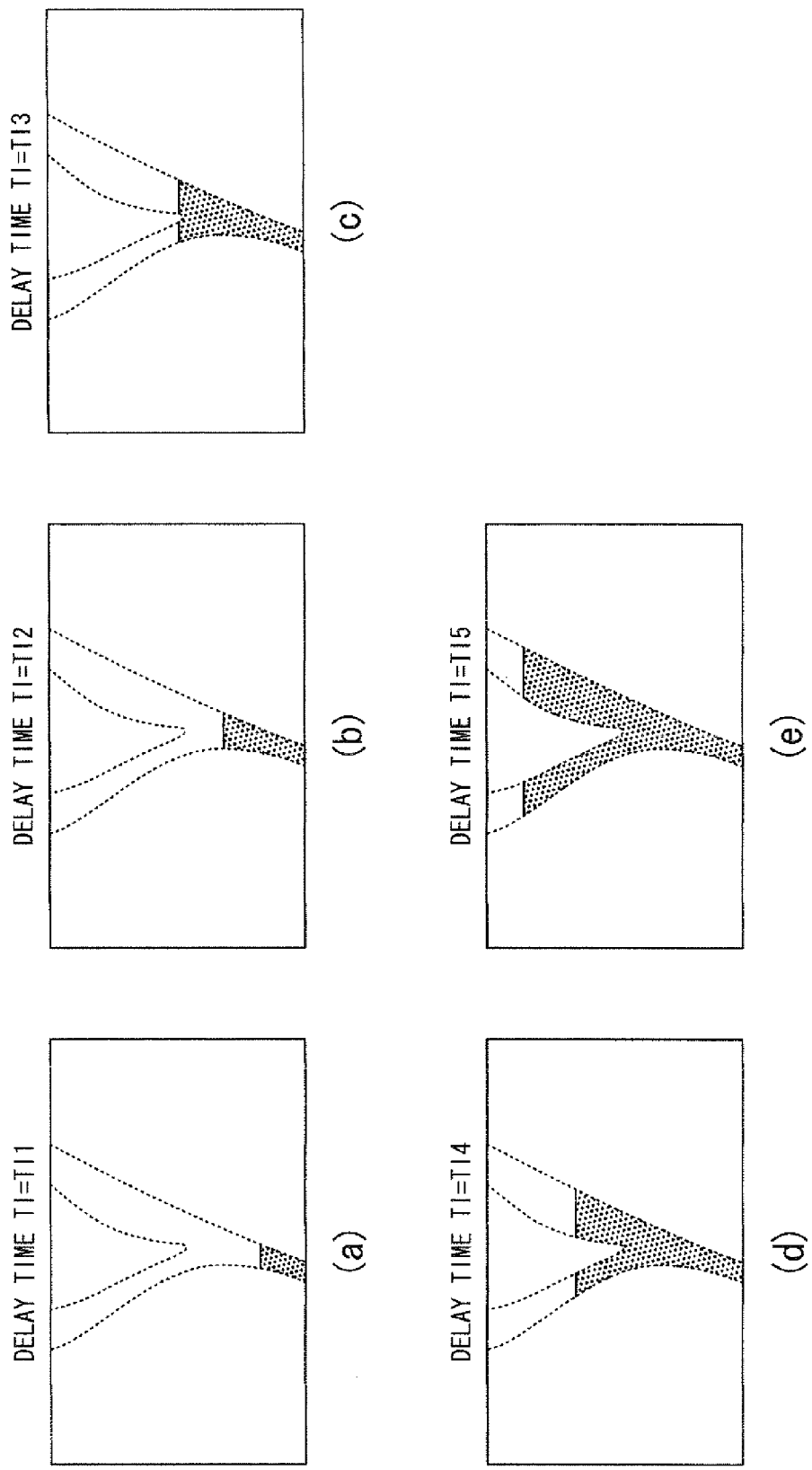
FIG. 7 shows schematic blood flow images acquired for different delay times arranged in ascending order of the delay time.

FIGS. 6 and 7 are schematic diagrams for illustrating a method of creating the blood flow image described above in the magnetic resonance imaging apparatus 20 shown in FIG. 1.

FIG. 6(a) shows a state of the blood flow immediately after application of the region-selective SAT pulse, and FIG. 6(b) shows a state of the blood flow created from data acquired the delay time TI after the application of the SAT pulse. The SAT pulse is applied to the data acquisition region shown in FIGS. 6(a) and 6(b). The longitudinal magnetization of the suppression target tissues (unwanted tissues) in the data acquisition region starts to be recovered after the application of the SAT pulse. However, at the time of data acquisition, the longitudinal magnetization is suppressed to substantially zero because of the application of the region-non-selective IR pulses as shown in FIG. 6(b).

On the other hand, the SAT pulse is not applied to the blood flow outside the data acquisition region, and thus the blood flow has a high longitudinal magnetization even after the application of the SAT pulse. Although the blood flow outside the data acquisition region has its polarity changed by the region-non-selective IR pulses applied following the SAT pulse, the blood flow still maintains a relatively high longitudinal magnetization when data acquisition starts. As described above, the periods from the times of application of the region-non-selective IR pulses to the time of start of data acquisition (that is, the optimal inversion times thereof) are determined not to eliminate the longitudinal magnetization of the blood externally flowing into the data acquisition region but to eliminate the longitudinal magnetization of the suppression target tissues (unwanted tissues). Therefore, the longitudinal magnetization of the blood externally flowing into the data acquisition region is not eliminated and is relatively high when data acquisition starts. As a result, in the image shown in FIG. 6(b), the blood flow is emphasized, and the unwanted tissues are suppressed.

FIG. 7 includes schematic blood flow images created for a plurality of different delay times TI. FIGS. 7(a) to (e) are blood flow images created for five delay times (TI1 to TI5) arranged in ascending order of the delay time TI. In these blood flow images, the range of the inflow blood varies with the delay time TI. In each blood flow image, the background signals are suppressed by application of the region-non-selective IR pulses. In addition, unlike the prior art, the plurality of blood flow images displayed are not created by performing subtraction between the labeled image data and the non-labeled image data acquired at the different times. Therefore, the effect of the suppression of the background signals does not deteriorate because of a motion of the subject body or a misregistration due to subtraction. Thus, the operator can easily observe the temporal change of the blood flow.

In addition, in order to further suppress the background signals, a subtraction processing can be performed between blood flow image data for a reference delay time TI and blood flow image data for the other delay times TI. For example, the background signals can be further suppressed by performing subtraction of the signal value of the blood flow image data for the longest delay time TI from the signal values of the blood flow image data for the other delay times TI.

In addition, if a subtraction processing is performed between the blood flow image data for adjacent delay times TI, the movement of the blood during the period corresponding to the difference between the adjacent delay times TI can be extracted.

Figure 8:
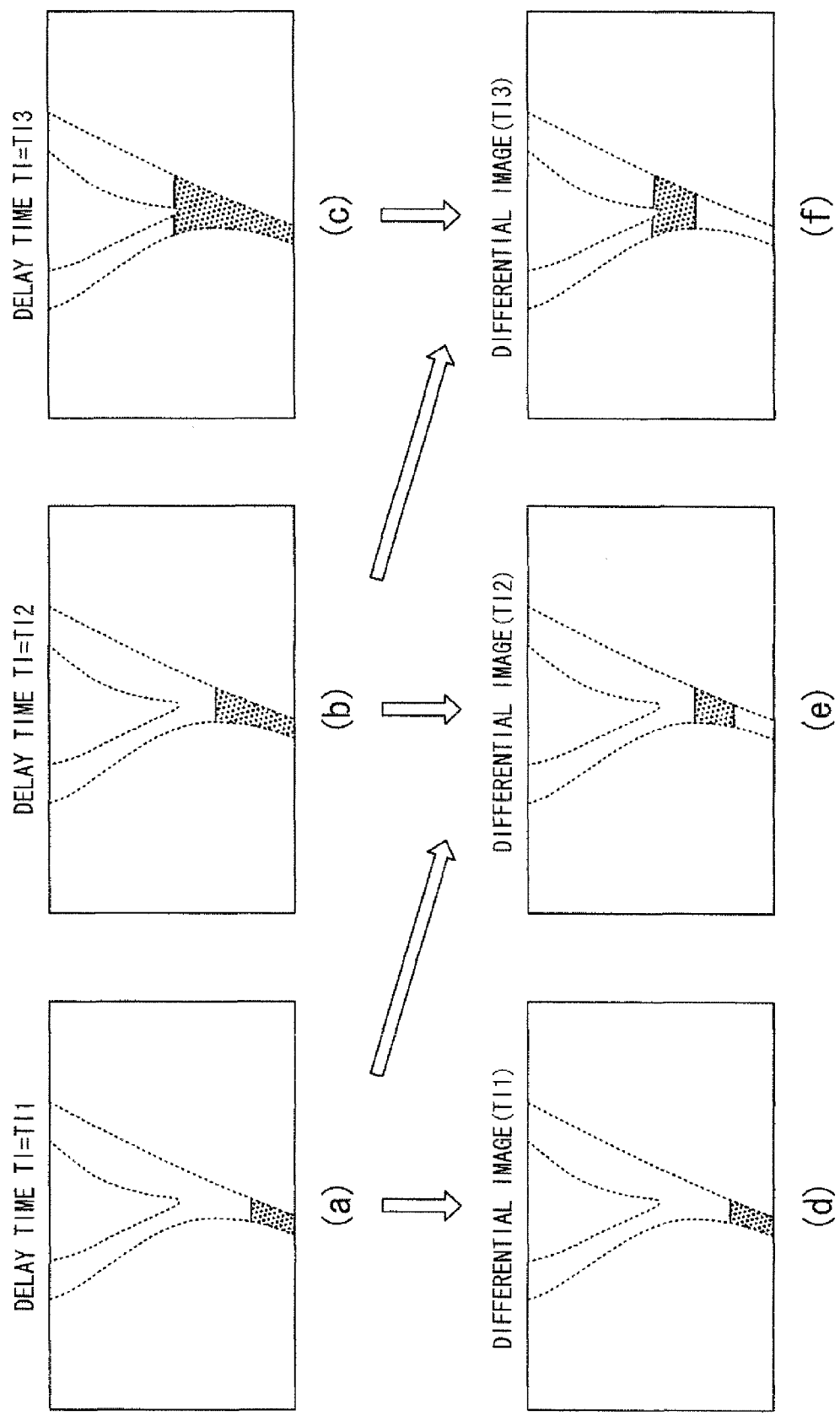
FIG. 8 is a first diagram for illustrating a concept of creating differential blood flow images from a plurality of blood flow images for different delay times.
Figure 9:
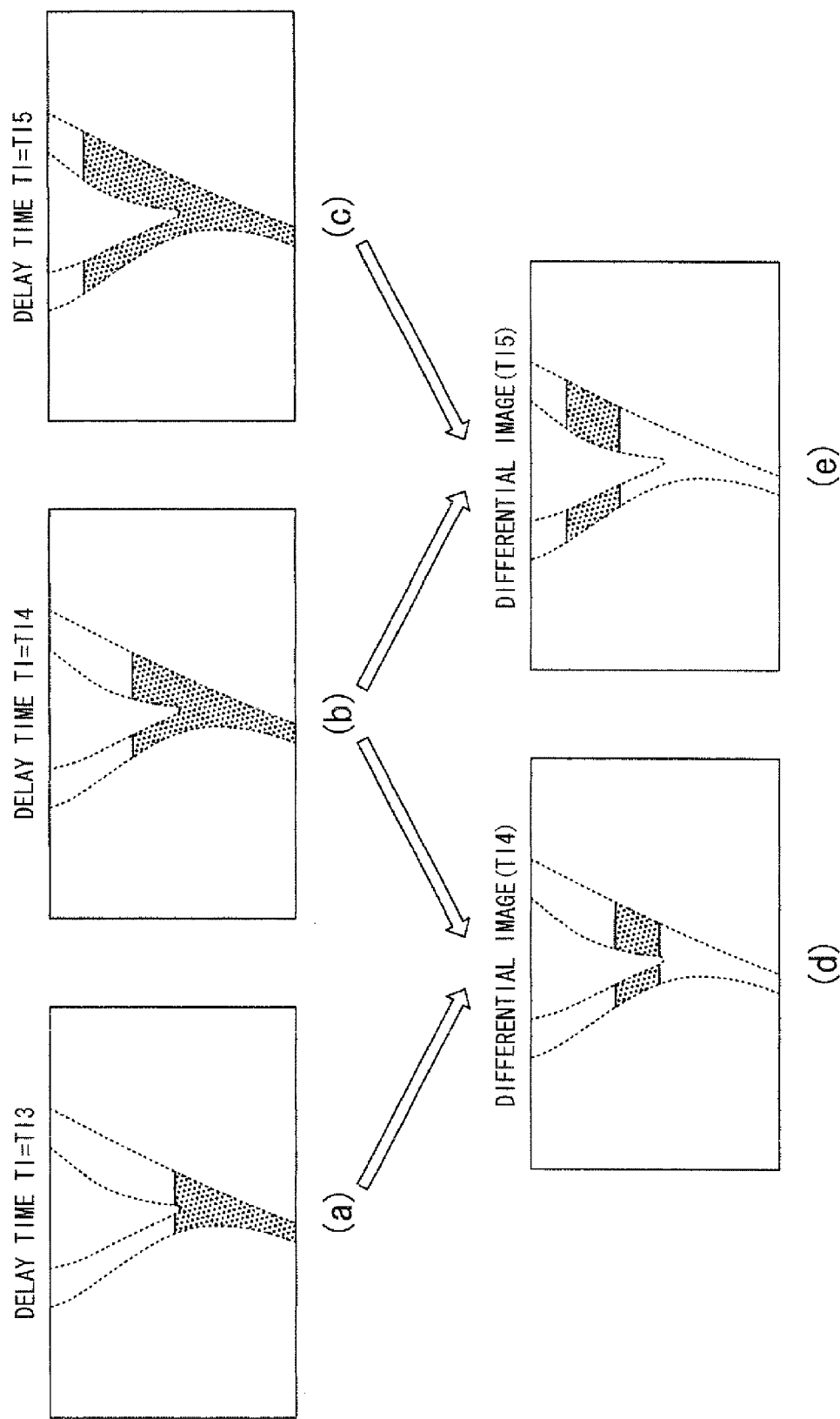
FIG. 9 is a second diagram for illustrating the concept of creating differential blood flow images from a plurality of blood flow images for different delay times.
Figure 10:
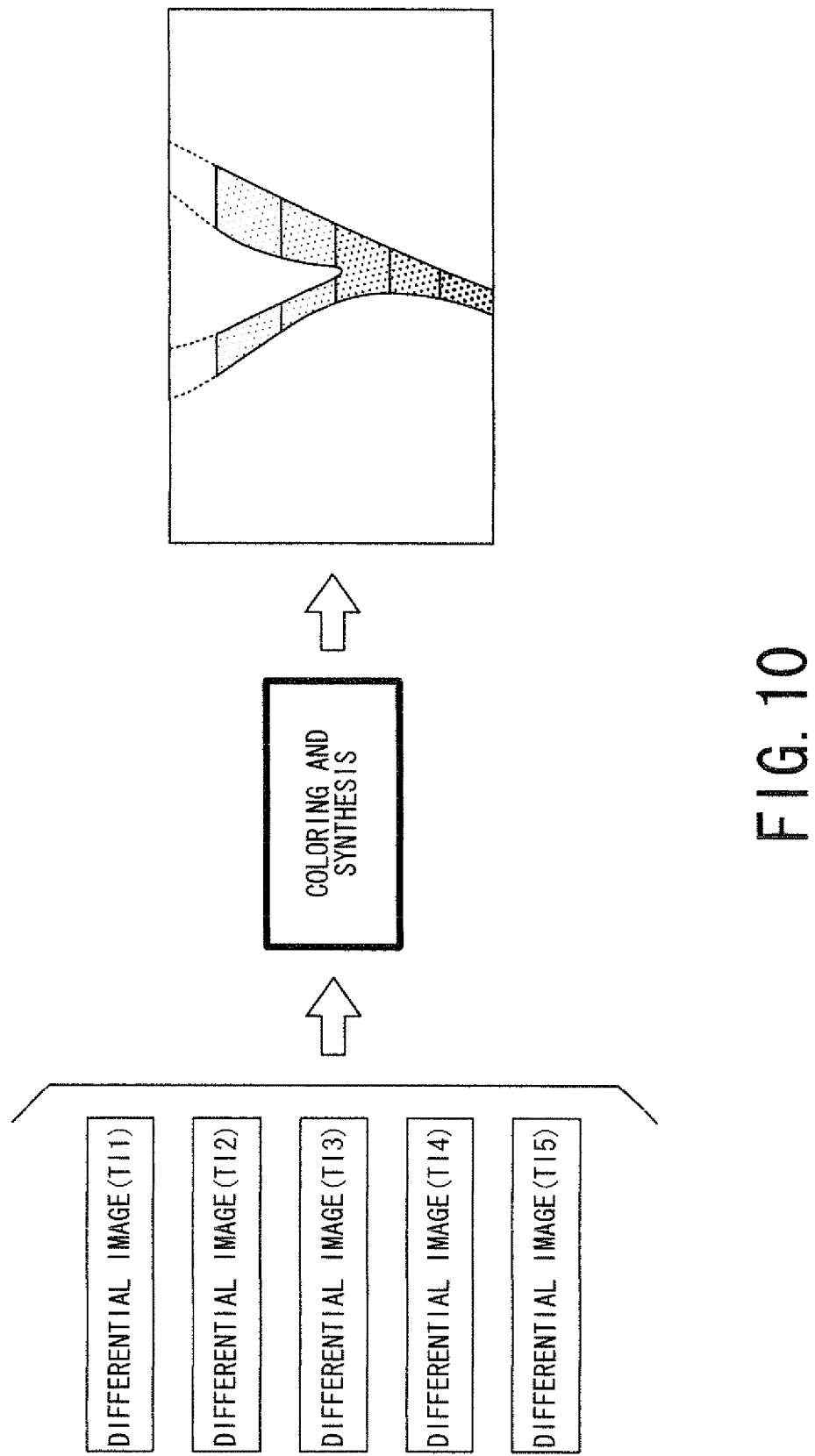
FIG. 10 is a diagram for illustrating a concept of creating a pseudo dynamic blood flow image by synthesizing a plurality of differential blood flow images differently colored.

FIGS. 8 and 9 are schematic diagrams showing a concept of the subtraction processing between the adjacent delay times TI. For example, five differential blood flow images (TI1 to TI5) (FIGS. 8(d), 8(e), 8(f), 9(d) and 9(e)) can be created from five blood flow images acquired for different delay times TI (FIGS. 8(a), 8(b), 8(c), 9(b) and 9(c)) by performing subtraction between blood flow images for adjacent delay times. Then, as shown in FIG. 10, a single composite pseudo-dynamic blood flow image that indicates the temporal change of the blood flow can be formed by superimposing the differential blood flow images TI1 to TI5 differently colored or shaded to facilitate visual distinction, for example. In other words, dynamic blood flow image data that visualizes a blood flow in a pseudo manner is created by synthesizing the plurality of pieces of the differential blood flow image data in such a manner that blood flow images represented by the differential blood flow image data are separately identified in terms of delay time.

Thus, the operator does not need to see a plurality of blood flow images to observe the temporal change of the blood flow but can observe the temporal change of the blood flow in one blood flow image.

(Modifications)

Figure 11:
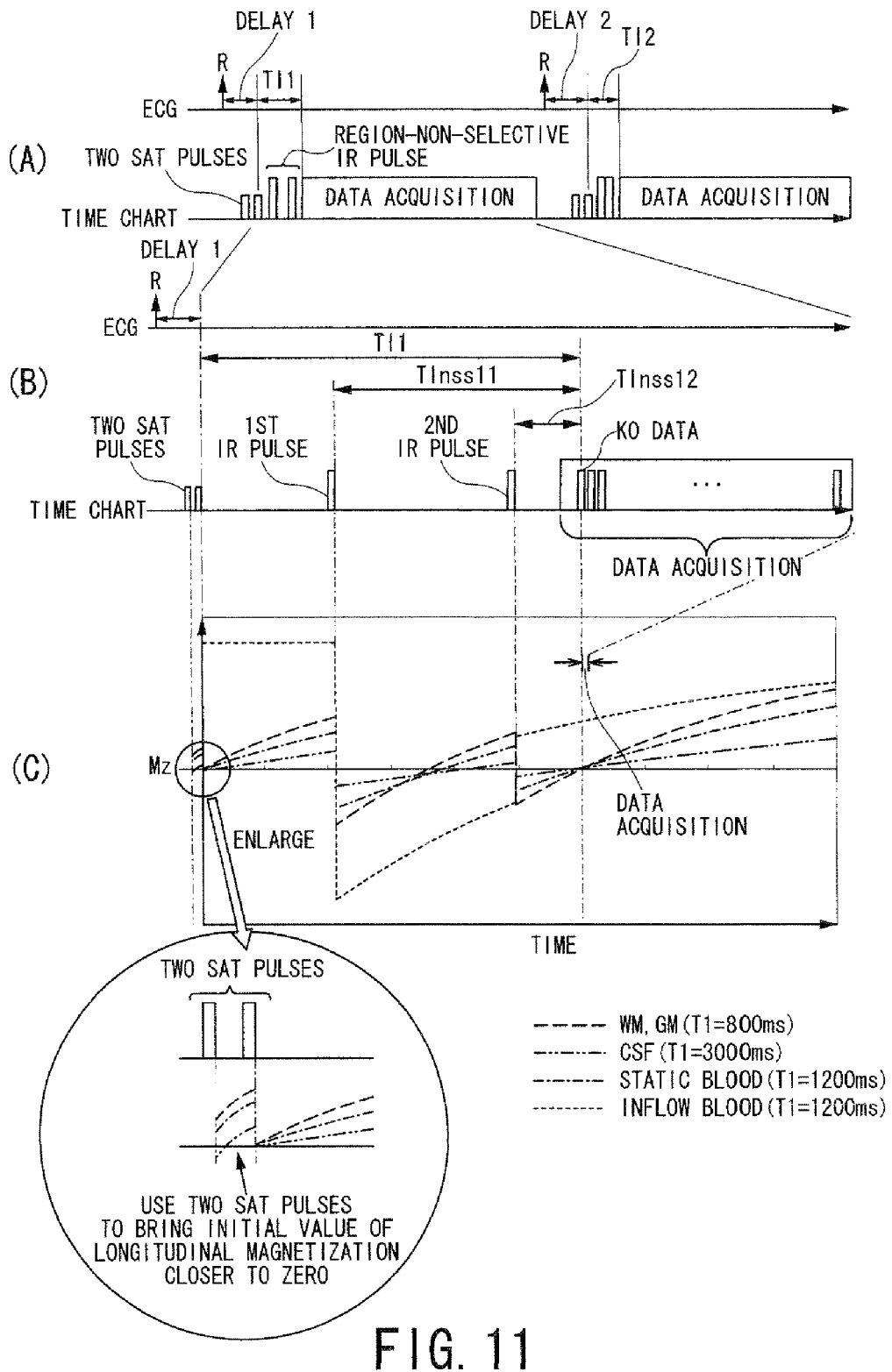
FIG. 11 includes diagrams for illustrating a pulse sequence and a temporal change in longitudinal magnetization according to a first modification of the embodiment.

FIG. 11 includes pulse sequence diagrams and a diagram for illustrating a change in longitudinal magnetization according to a first modification of the embodiment described above. FIG. 11 differs from FIG. 4 in that a second saturation (SAT) pulse is applied immediately after application of the SAT pulse. In the embodiment described above, on the assumption that the longitudinal magnetization of all the unwanted constituents is reduced to zero by the application of the SAT pulse, the optimal inversion times of the region-non-selective IR pulses are determined to cause the longitudinal magnetization of the unwanted constituents to become again zero when data acquisition starts the delay time TI after the application of the SAT pulse.

However, in actual, applying one SAT pulse may not suffice for completely reducing the longitudinal magnetization of the unwanted constituents to zero at the time of application of the SAT pulse. Consequently, the longitudinal magnetization of the unwanted constituents is not reduced to zero also at the start of data acquisition. In particular, the deviation from zero increases as the delay time TI becomes longer.

To solve the problem, according to the first modification, a second saturation (SAT) pulse is applied immediately after the application of the SAT pulse (alternatively, a larger number of SAT pulses may be applied), thereby bringing the initial value of the longitudinal magnetization of the unwanted constituents closer to zero. As a result, the longitudinal magnetization of the unwanted constituents at the start of data acquisition can be brought close to zero with higher reliability.

Figure 12:
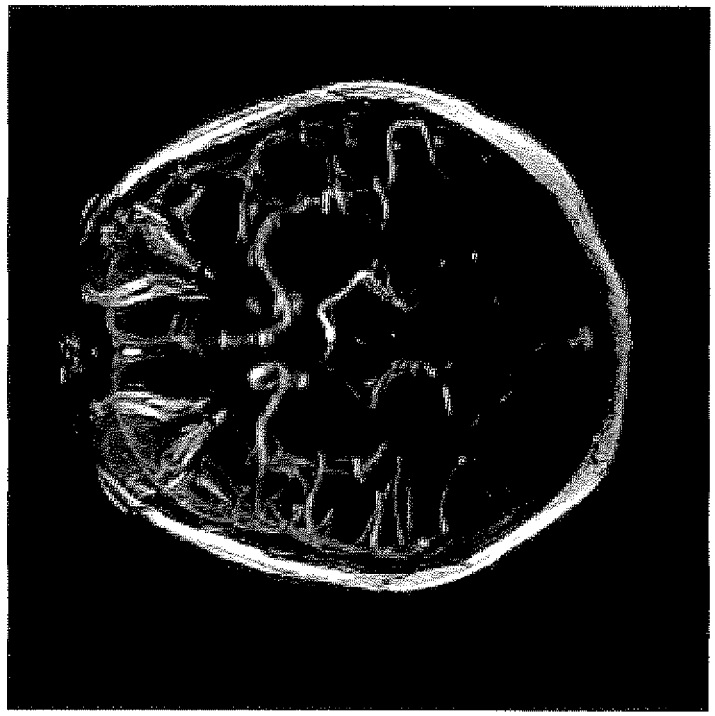
FIG. 12 includes diagrams showing an example of an actual image that illustrates the effect of the first modification.
Figure 12:
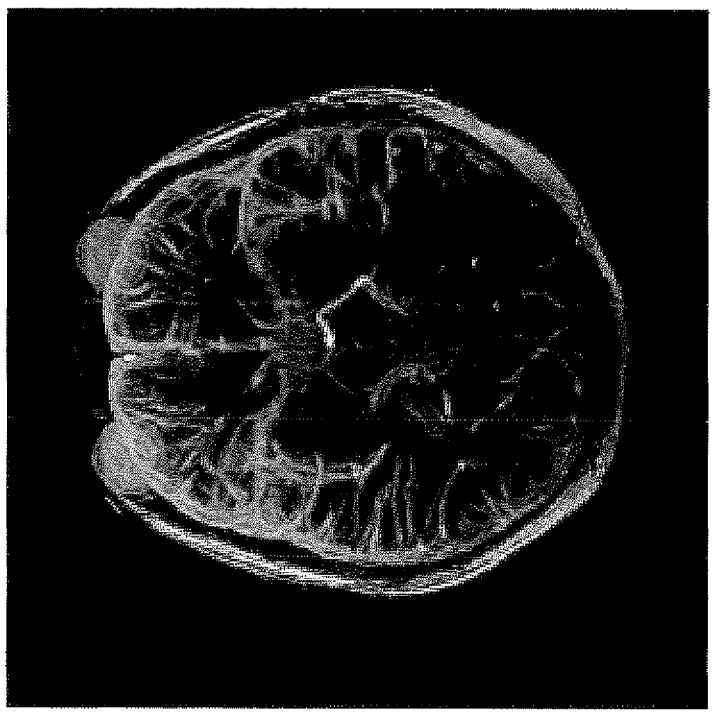

FIG. 12 shows an example of actual head images (showing the blood flow). FIG. 12(A) is a blood flow image acquired by applying a single SAT pulse, and FIG. 12(B) is a blood flow image acquired by applying the second SAT pulse immediately after application of the SAT pulse. From comparison between FIGS. 12(A) and 12(B), it can be confirmed that the background signals are more satisfactorily suppressed in the blood flow image acquired by applying the second SAT pulse immediately after application of the SAT pulse.

Figure 13:
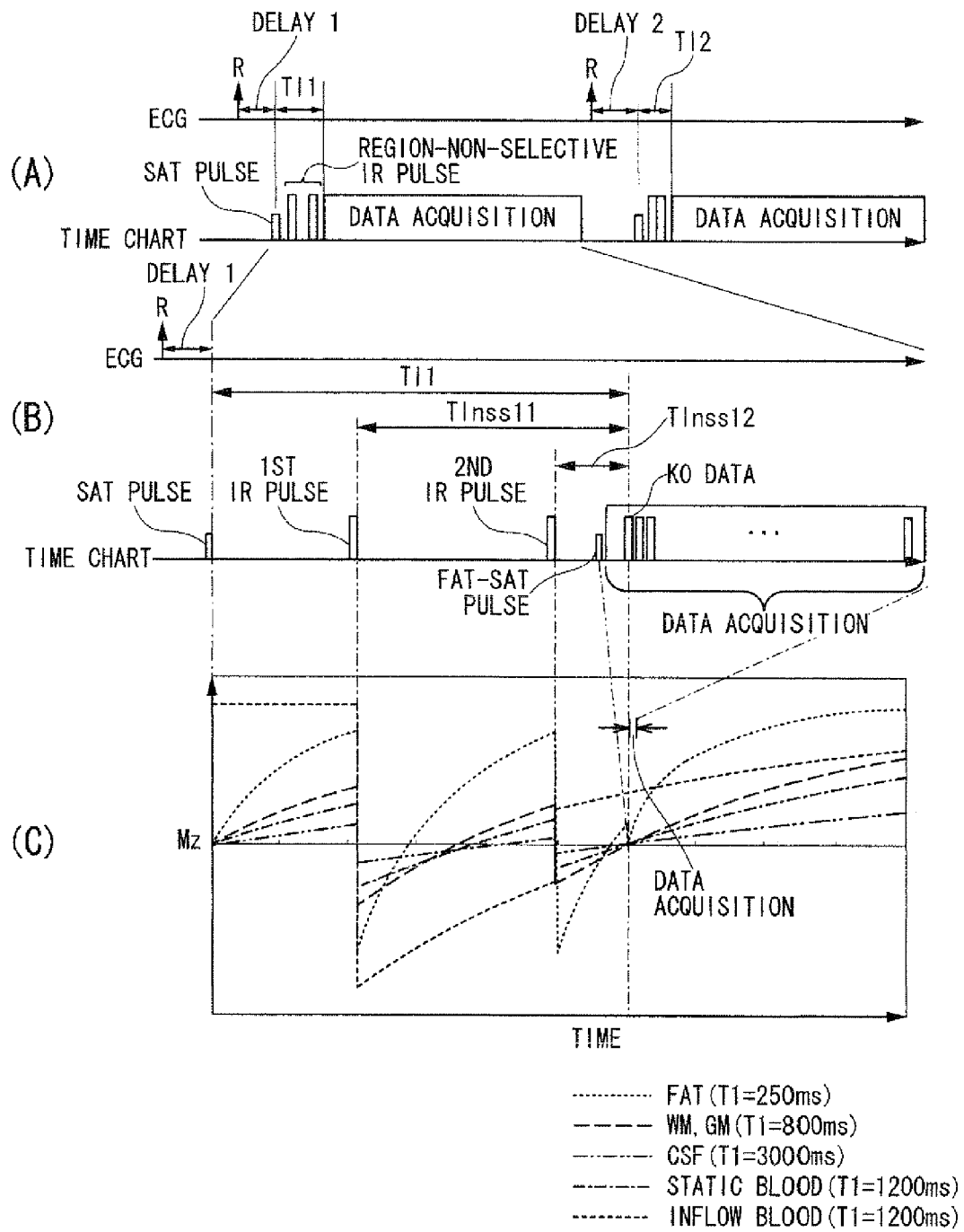
FIG. 13 includes diagrams for illustrating a pulse sequence and a temporal change in longitudinal magnetization according to a second modification of the embodiment.

FIG. 13 includes pulse sequence diagrams and a diagram for illustrating a change in longitudinal magnetization according to a second modification of the embodiment described above. FIG. 13 differs from FIG. 4 in that a fat saturation (FAT-SAT) pulse is applied immediately before start of data acquisition.

In the case where the unwanted constituents include fat, the longitudinal magnetization of fat can be suppressed by applying a frequency-selective FAT-SAT pulse. In FIG. 13(C), a change in longitudinal magnetization of fat (of a longitudinal relaxation time T1 of 250 ms) is shown by a thin dotted line.

According to the second modification, the background signals involved with fat are suppressed by applying the FAT-SAT pulse, whereas the background signals involved with the unwanted constituents other than fat (white matter, gray matter, CSF) are suppressed by optimizing the inversion times of the region-non-selective IR pulses. If the background signals involved with all the unwanted constituents including fat are to be suppressed by the region-non-selective IR pulses, the required number of region-non-selective IR pulses can increase, and thus the measurement time can also increase. However, according to the second modification, the background signals involved with fat can be suppressed by the FAT-SAT pulse, so that the measurement time can be reduced.

According to the pulse sequences shown (FIGS. 4, 11 and 13) in the above description, application of the region-selective saturation (SAT) pulse, application of the region-non-selective IR pulses, and data acquisition are performed in synchronization with a signal (ECG signal) that represents the pulsation. However, the synchronization with the signal (ECG signal) that represents the pulsation is not essential for the present invention, and the present invention can be applied to a case where the ECG signal is omitted from the pulses sequences shown in FIGS. 4, 11 and 13. Even in this case, the present invention provides the same effects as those described above.

As described above, according to this embodiment and the modifications thereof, the magnetic resonance imaging apparatus 20 can acquire an MRA image in which a background signal is suppressed and a temporal change of a blood flow can be observed without using a contrast medium. In addition, an image used for subtraction, which would conventionally be necessary to suppress the background signal, is not necessary, so that the imaging time can be reduced. Furthermore, owing to the display processing, a temporal change of a blood flow can be observed in a single image.

What is claimed is:

1. A magnetic resonance imaging apparatus, comprising:
   a data acquiring unit that acquires a plurality of pieces of magnetic resonance data respectively associated with a plurality of different delay times according to a pulse sequence in which (a) a region-selective saturation pulse is first applied to a first region, (b) a region-non-selective inversion recovery pulse is then applied to a second region, and (c) then the magnetic resonance data is acquired, the delay time being defined as a period from a time of saturation pulse application to start of magnetic resonance data acquisition, the second region including and being larger than the first region; and
   a blood flow image creating unit that creates a plurality of pieces of blood flow image data also respectively associated with the plurality of different delay times, using the acquired magnetic resonance data.

2. The magnetic resonance imaging apparatus according to claim 1, wherein:
   the data acquiring unit applies the region-non-selective inversion recovery pulse a plurality of times between the time of saturation pulse application and the start of magnetic resonance data acquisition.

3. The magnetic resonance imaging apparatus according to claim 2, wherein:
   the data acquiring unit applies the region-non-selective inversion recovery pulse twice between the time of saturation pulse application and the start of magnetic resonance data acquisition.

4. The magnetic resonance imaging apparatus according to claim 1, further comprising:
   a parameter storage unit that stores an optimal inversion time, which is a period from a time of the region-non-selective inversion recovery pulse application to the start of magnetic resonance data acquisition, for each of the plurality of delay times,
   wherein the data acquiring unit sets the period from the time of the region-non-selective inversion recovery pulse application to the start of magnetic resonance data acquisition by referring to the stored optimal inversion time.

5. The magnetic resonance imaging apparatus according to claim 4, wherein:
   the optimal inversion time is determined to minimize longitudinal magnetization of a target tissue to be suppressed excluding an inflow blood at the start time of magnetic resonance data acquisition, based on the set delay time and the longitudinal relaxation time of the target tissue to be suppressed.

6. The magnetic resonance imaging apparatus according to claim 4, wherein:
   the region-non-selective inversion recovery pulse is applied a plurality of times between the time of the saturation pulse application and the start magnetic resonance data acquisition, and the optimal inversion time of each region-non-selective inversion recovery pulse is determined to minimize magnitudes of longitudinal magnetizations for each of a plurality of target tissues to be suppressed, based on the set delay time and longitudinal relaxation times of each of the plurality of target tissues to be suppressed.

7. The magnetic resonance imaging apparatus according to claim 1, wherein:
   the data acquiring unit acquires the magnetic resonance data in synchronization with a pulsation of a subject body so that the time period between occurrence of a reference signal derived from the pulsation and start of magnetic resonance data acquisition is set to be constant.

8. The magnetic resonance imaging apparatus according to claim 7, wherein:
   the data acquiring unit acquires the magnetic resonance data so that the time period between the reference signal occurrence and the start of k-space data acquisition for a center of k-space is constant.

9. The magnetic resonance imaging apparatus according to claim 1, wherein:
   the blood flow image creating unit creates the plurality of pieces of blood flow image data for display by performing subtraction processing between (a) blood flow image data associated with a reference delay time and (b) blood flow image data associated with the other delay times of the plurality of pieces of blood flow image data.

10. The magnetic resonance imaging apparatus according to claim 1, wherein the blood flow image creating unit creates:

a plurality of pieces of differential blood flow image data associated with the plurality of delay times, by performing subtraction between pieces of blood flow image data associated with adjacent delay times, and further creates dynamic blood flow image data that visualizes blood flow in a pseudo manner by synthesizing the plurality of pieces of differential blood flow image data so that blood flow images represented by the differential blood flow image data are separately identified in terms of their respective different delay times.

11. The magnetic resonance imaging apparatus according to claim 1, wherein:
the data acquiring unit acquires the magnetic resonance data after applying a fat suppression pulse immediately before acquiring the magnetic resonance data.

12. The magnetic resonance imaging apparatus according to claim 1, wherein:
the data acquiring unit acquires the magnetic resonance data after applying a second region-selective saturation pulse immediately after the earlier-applied region-selective saturation pulse.

13. The magnetic resonance imaging apparatus according to claim 1, wherein the data acquisition unit applies the region-selective saturation pulse and the region-non-selective inversion recovery pulse at times such that signals from tissues, other than a blood signal, to be suppressed are selectively suppressed.

14. A control method of a magnetic resonance imaging apparatus, the method comprising:
acquiring a plurality of pieces of magnetic resonance data respectively associated with a plurality of different delay times according to a pulse sequence in which (a) a region-selective saturation pulse is first applied to a first region, (b) a region-non-selective inversion recovery pulse is then applied to a second region, and (c) then the magnetic resonance data is acquired, the delay time being defined as a period from a time of saturation pulse application to start of magnetic resonance data acquisition, the second region including and being larger than the first region; and creating a plurality of pieces of blood flow image data associated with the plurality of different delay times using the magnetic resonance data.

15. A magnetic resonance imaging apparatus, comprising:
a data acquiring unit that acquires a plurality of pieces of magnetic resonance data according to a pulse sequence in which (a) a region-selective saturation pulse is first applied to a first region, (b) a region-non-selective inversion recovery pulse is then applied to a second region, and (c) then the magnetic resonance data is acquired, the second region including and being larger than the first region; and a blood flow image creating unit that creates a plurality of pieces of blood flow image data using the acquired magnetic resonance data.

16. The magnetic resonance imaging apparatus according to claim 15, wherein the data acquisition unit applies the region-selective saturation pulse and the region-non-selective inversion recovery pulse at times such that signals from tissues, other than a blood signal, to be suppressed are selectively suppressed.

17. The magnetic resonance imaging apparatus according to claim 16, wherein the data acquisition unit determines a number of the region-non-selective inversion recovery pulses to be used such that signals from tissues, other than a blood signal, to be suppressed other than a blood signal are selectively suppressed.

18. The magnetic resonance imaging apparatus according to claim 17, wherein the data acquisition unit applies the region-non-selective inversion recovery pulses at times such that signals from tissues, other than a blood signal, to be suppressed are selectively suppressed.

* * * * *